(12) United States Patent
Moldawski et al.

(10) Patent No.: US 7,581,545 B1
(45) Date of Patent: Sep. 1, 2009

(54) DERMABRASIVE DEVICE

(76) Inventors: Clerice Moldawski, 1101 Whispering Cove, N. Myrtle Beach, SC (US) 29582; Robert Moldawski, 1101 Whispering Cove, N. Myrtle Beach, SC (US) 29582

( * ) Notice: Subject to any disclaimer, the term of this patent is extended or adjusted under 35 U.S.C. 154(b) by 370 days.

(21) Appl. No.: 11/606,593

(22) Filed: Nov. 30, 2006

(51) Int. Cl.
*A45D 29/18* (2006.01)

(52) U.S. Cl. .............. 132/76.4; 132/75.8; 132/73.6; 604/290; 606/131

(58) Field of Classification Search ............ 606/131; 132/73.6; 433/166; 451/539; 7/118, 120
See application file for complete search history.

(56) References Cited

U.S. PATENT DOCUMENTS

| | | | |
|---|---|---|---|
| 1,709,437 A * | 4/1929 | Lacoste et al. ......... 248/292.14 |
| 2,056,379 A * | 10/1936 | Acocella .................. 132/73.6 |
| 3,636,625 A | 1/1972 | Pracht | |
| 3,932,908 A | 1/1976 | Bitgood et al. | |
| D249,565 S * | 9/1978 | Levin ........................... D28/58 |
| 5,109,315 A * | 4/1992 | Morse ......................... 361/42 |
| D339,275 S | 9/1993 | Fukuda et al. | |
| 5,819,757 A * | 10/1998 | Baekkelund ............... 132/73.6 |
| 6,178,970 B1 * | 1/2001 | Purifoy et al. ............. 132/76.4 |
| 6,363,944 B1 | 4/2002 | Stangenberg | |
| 6,523,546 B2 | 2/2003 | Jo et al. | |
| 6,848,451 B2 | 2/2005 | Postal et al. | |
| 6,911,031 B2 * | 6/2005 | Muldner .................... 606/131 |
| 7,028,362 B2 | 4/2006 | Davallou | |
| 7,044,938 B2 * | 5/2006 | La Bianco et al. .......... 604/290 |
| 7,093,603 B2 | 8/2006 | Han | |
| 2004/0167481 A1 * | 8/2004 | Carlucci et al. ............. 604/291 |
| 2005/0091867 A1 * | 5/2005 | Andis et al. ................... 34/96 |

* cited by examiner

*Primary Examiner*—Robyn Doan
*Assistant Examiner*—Brianne E O'Neill
(74) *Attorney, Agent, or Firm*—P. Jeff Martin; The McGougan Law Firm, LLC

(57) ABSTRACT

A lightweight, portable, electrically-powered dermabrasive device adapted to gently and painlessly remove keratinized epidermal portions of the hands and feet. The dermabrasive device includes a protective shield which shields user against contact from flakes of flying or ejected epidermis or other detritus.

17 Claims, 7 Drawing Sheets

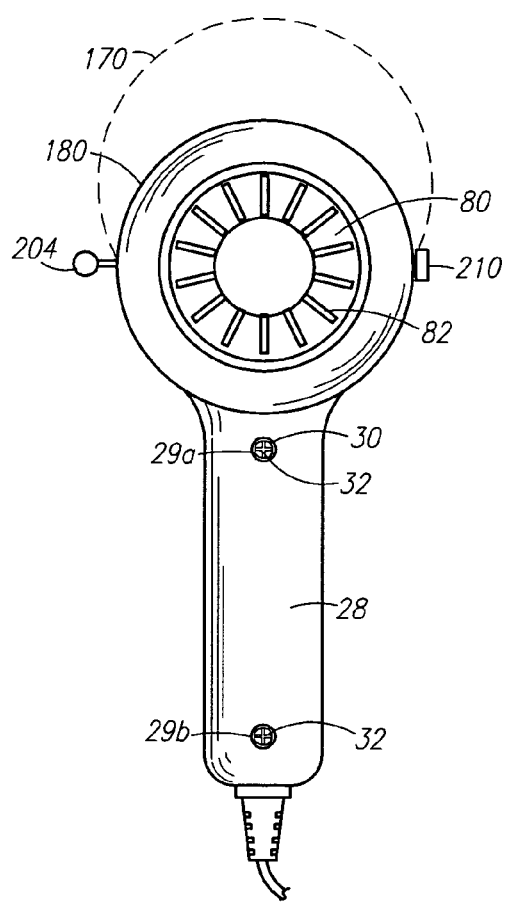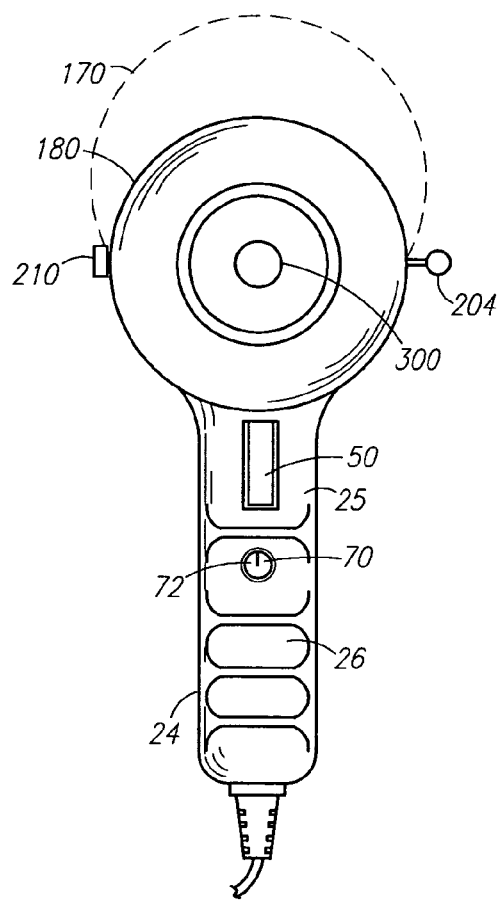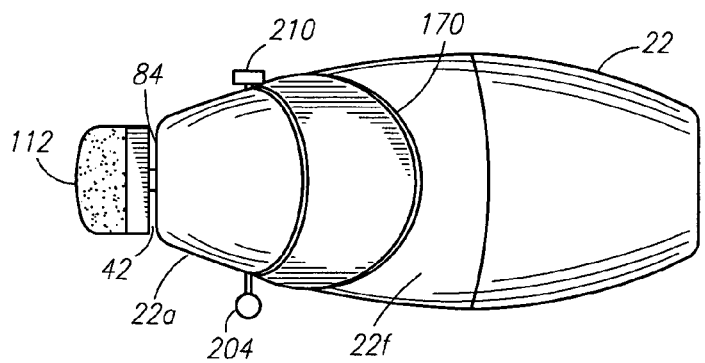

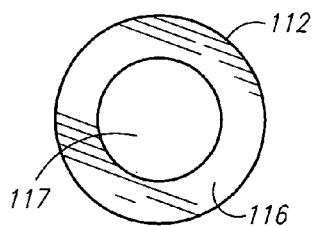
Fig. 5
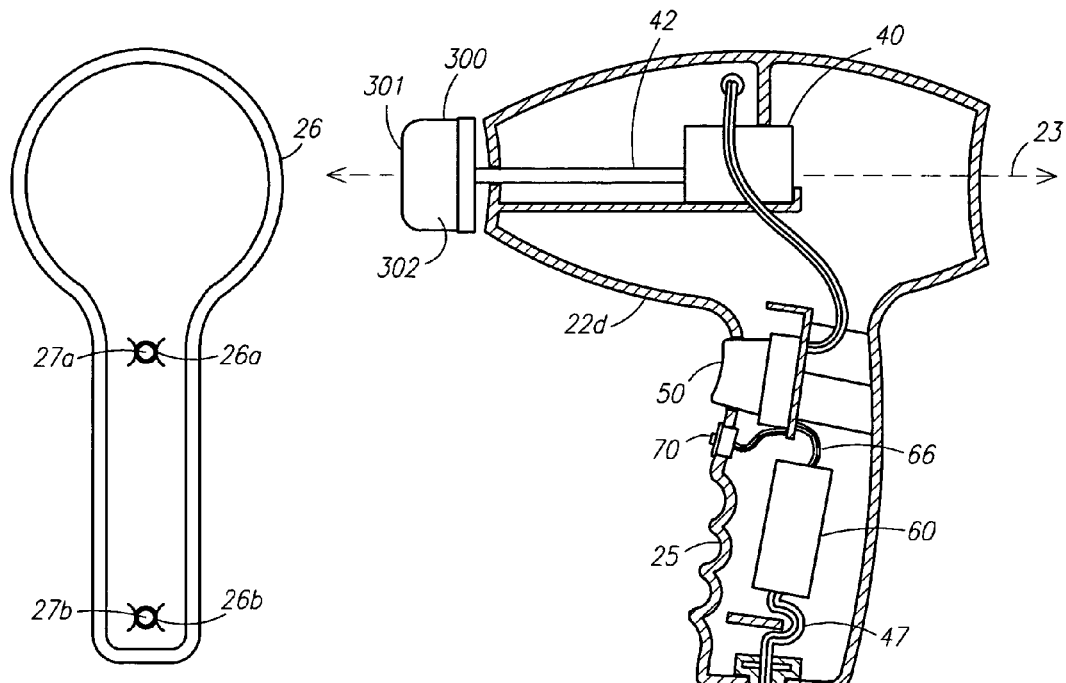
Fig. 6
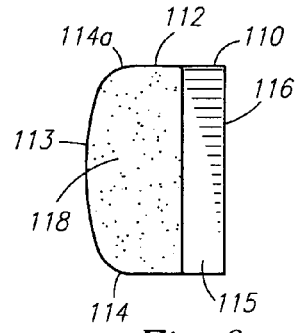
Fig. 7
Fig. 8
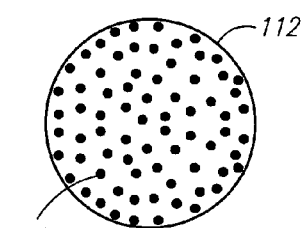
Fig. 9
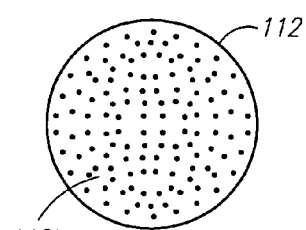
Fig. 10
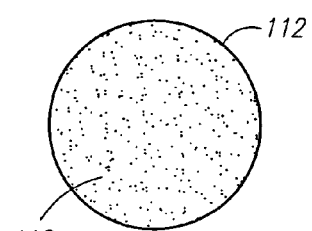
Fig. 11

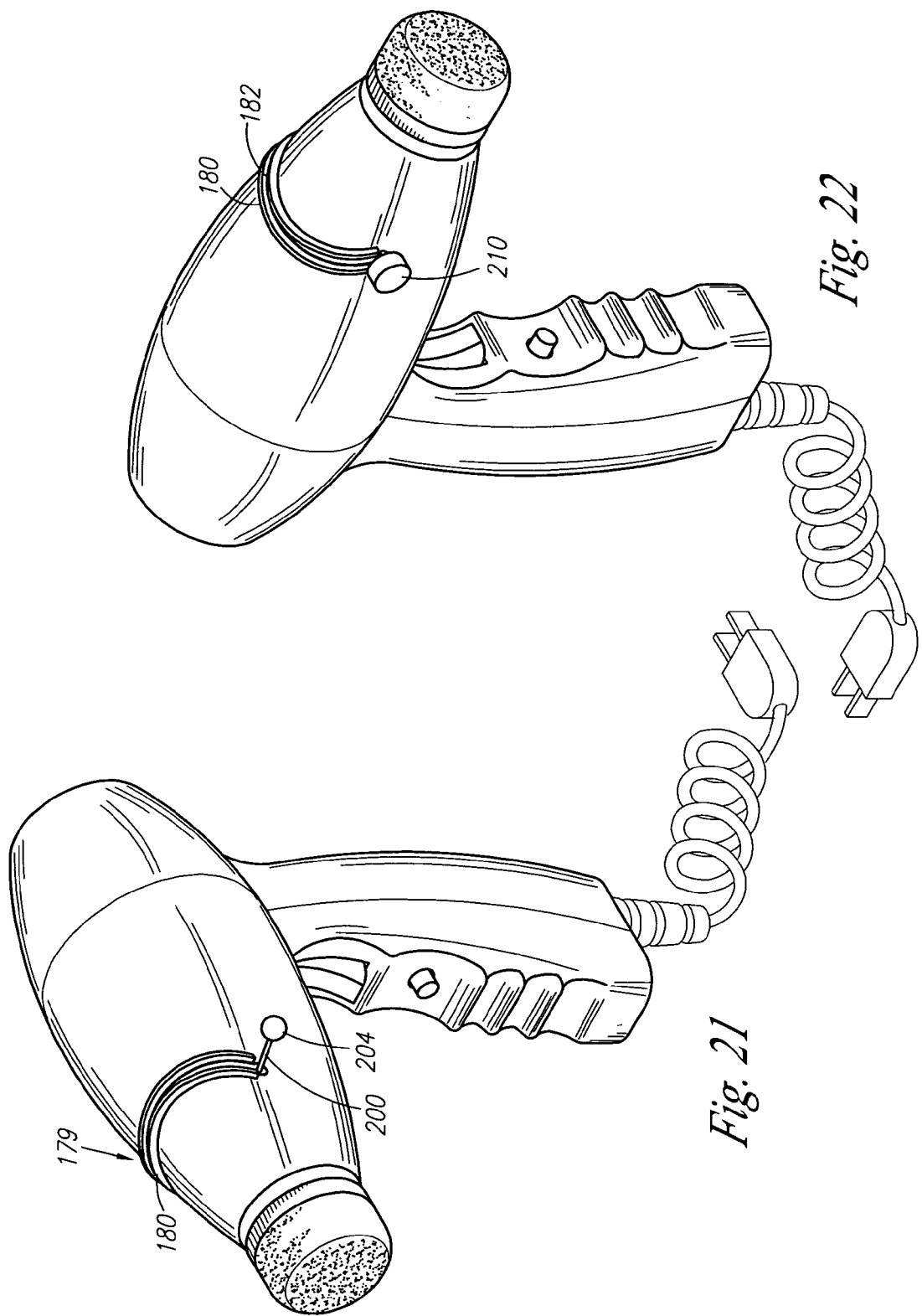

DERMABRASIVE DEVICE

RELATED APPLICATIONS

The present invention was first described in Disclosure Document No. 606,969 filed on Oct. 2, 2006 under 35 U.S.C. §122, 37 C.F.R. §1.14, and MPEP §1706. It is respectfully requested that said Disclosure Document remain a permanent part of the file history of the present application and be relied upon during the pending prosecution, and for any other matters that may arise concerning said present application and the subject matter contained therein. There are no previously filed, nor currently any co-pending applications, anywhere in the world.

BACKGROUND OF THE INVENTION

1. Field of the Invention

The present invention relates generally to scrubbing devices and, more particularly, to a lightweight, portable, electrically-powered dermabrasive device.

2. Description of the Related Art

Calluses and corns are areas of thick, hardened, dead skin. They form to protect the skin and body structure under the skin from pressure, friction, and injury. Calluses generally form on the palms of the hands or the soles of the feet when the epidermis thereof becomes partially keratinized due to repeated pressure or friction on an area of skin overtime. The pressure causes the skin to die and form a hard, protective surface.

Calluses on the hands are often caused by the regular handling of an object that puts pressure on the hand, such as tools or sports equipment. Calluses and corns on the feet are often caused by pressure from footwear such as tight shoes, high-heeled shoes, loose shoes, and thin-sole shoes. Walking barefoot can also cause calluses.

Calluses and corns can cause discomfort and can also become painful. Thus, it is often necessary to periodically remove such calluses from the palms of the hands or soles of the feet. Traditionally, a pumice stone or a sander device have been employed for manually filing the calluses and corns in order to facilitate their removal. However, these conventional methods and apparatuses for callus removal are time consuming, laborious, inefficient, and often painful. In addition, the prior art devices have failed to provide a means for shielding user against contact from flakes of flying or ejected epidermis.

Accordingly, a need has arisen for in a lightweight, portable, electrically-powered dermabrasive device adapted to gently and painlessly remove keratinized epidermal portions of the hands and feet in a manner which is quick, easy, and efficient. The development of the dermabrasive device fulfills this need.

A search of the prior art did not disclose any patents that read directly on the claims of the instant invention; however, the following references were considered related.

U.S. Pat. No. 6,848,451 B2, issued in the name of Postal et al. discloses a tool assembly having a head that imparts oscillatory motion to a desired device coupled to the assembly, wherein tool assembly is particularly advantageous when used in connection with massaging, dermabrasion, nail buffing and sculpting, woodworking, and polishing assemblies.

U.S. Pat. No. 4,440,182, issued in the name of Holm discloses an orbital sanding instrument which is especially useful for processing artificial fingernails.

U.S. Pat. No. 3,932,908, issued in the name of Bitgood et al. discloses a portable scrubbing device in which a detachable rotary scrub brush is fitted to a handle member linked by a flexible drive cable to a motor in the housing of the device.

U.S. Pat. No. 6,523,546 B2, issued in the name of Joe et al. discloses a pedicure sander having a shock-absorbing unit utilized for removal of calluses or corns from the hands or feet.

U.S. Pat. No. Des. 339,275 issued in the name of Fukuda et al. discloses the ornamental design for a portable electric sander.

U.S. Pat. No. 7,093,603 B2, issued in the name of Han discloses a vacuum skin treating implement for removing calluses of the skin.

U.S. Pat. No. 6,363,944 B1, issued in the name of Stangenberg discloses an apparatus for removing calluses, especially in chiropody, comprising a handle and a functional element exchangeably arranged thereon.

U.S. Pat. No. 3,636,625, issued in the name of Pracht discloses an apparatus for removing calluses which includes a protective plate provided with an elongated handle, a cover plate and a cutting blade.

U.S. Pat. No. 7,028,362 B2, issued in the name of Davallou discloses a foot spraying and scrubbing device that is designed to conveniently and safely clean difficult areas of the foot such as between the toes.

Internet publication advertisement featuring an electric pedicure file provided at www.creative-equipment.com.

Internet publication advertisement featuring a powered pedicure tool provided at www.submarino.com.

Internet publication advertisement featuring a portable pedicure tool provided at www.taiff.com.

Consequently, a need has been felt for a lightweight, portable, electrically-powered dermabrasive device adapted to gently and painlessly remove keratinized epidermal portions of the hands and feet in a manner which is quick, easy, and efficient.

SUMMARY OF THE INVENTION

Therefore, it is an object of the present invention to provide an electrically-powered dermabrasive device adapted to gently and painlessly remove keratinized epidermal portions of the hands and feet.

It is another object of the present invention to provide a portable and lightweight dermabrasive device.

It is another object of the present invention to provide a dermabrasive device which can be operated by a user without experiencing joint or muscle pain.

It is another object of the present invention to provide a dermabrasive device available in a variety of colors.

It is another object of the present invention to provide a dermabrasive device being compact and durable.

It is still another object of the present invention to provide a manual speed selector which allows a user to select a variety of RPM motor speeds.

It is another object of the present invention to provide a plurality of disposable sanders.

It is another object of the present invention to provide sanders available in a variety of abrasive textures.

It is yet another object of the present invention to provide sanders being removably attachable to a head receiving component.

It is still another object of the present invention to provide a protective shield being angularly adjustable.

It is another object of the present invention to provide a ground fault circuit interrupter adapted to prevent a risk of electrocution in the event dermabrasive device is accidentally immersed in water.

Briefly described according to one embodiment of the present invention, a dermabrasive device is disclosed. The dermabrasive device is adapted to gently and painlessly remove keratinized epidermal portions of the hands and feet in a manner which is quick, easy, and efficient. The dermabrasive device comprises a portable housing which includes a barrel portion and a handle which are formed by a pair of abutting housing members that are connected by a fastening means.

The dermabrasive device further comprises an electric drive motor which rotatably drives a plurality of removably attachable heads defined as cap portions. The plurality of heads or cap portions each includes a layer of abrasive material bonded to the forward face thereof. The abrasive material is defined of various abrasive textures which includes coarse, medium, and fine. Thus, the plurality of heads includes at least one cap portion bonded with a coarse texture, at least one cap portion bonded with a medium texture, and at least one cap portion bonded with a fine texture.

An On/Off switch is provided on the sidewall of the handle for actuating the electric drive motor. A ground fault circuit interrupter is included and is adapted to prevent a risk of electrocution in the event dermabrasive device is accidentally immersed in water.

A controller switch is positioned below the On/Off switch and includes a manual speed selector adapted to allow a user to manually control revolutions per minute (RPM) speed of the electric drive motor. The manual speed selector has multiple settings such as low, medium, and high that can be selected by user to designate speed preference.

A disposable, protective shield is provided, wherein protective shield is adapted to shield user against contact from flakes of flying or ejected epidermis or other detritus as user operates the present invention. The protective shield is further adapted so as to be angularly adjustable via a shield adjustment mechanism.

An alternate embodiment of the present invention includes a push-button release mechanism adapted to facilitate release of cap portion from a hub. The push-button release mechanism is operationally and mechanically configured and adapted such that depression of the cap release button facilitates retraction of splines into the hub, thereby allowing the release and removal of cap portion from hub.

The use of the present invention allows for calluses on the palms of the hand and soles of the feet to be gently and painlessly removed in a manner which is quick, easy, and efficient.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 2 is a rear elevational view of the dermabrasive device, according to the preferred embodiment of the present invention;

FIG. 3 is a front elevational view of the dermabrasive device, according to the preferred embodiment of the present invention;

FIG. 4 is a topside view of the dermabrasive device, according to the preferred embodiment of the present invention;

FIG. 5 is a cutaway view of the dermabrasive device illustrating one abutting housing member removed to expose extensions in a second abutting housing member;

FIG. 6 is a cross-sectional view taken along lines VI-VI of FIG. 1 illustrating interior components;

FIG. 7 is a bottom plan view of a cap portion, according to the preferred embodiment of the present invention;

FIG. 8 is a side elevational view of the cap portion, according to the preferred embodiment of the present invention;

FIG. 9 is a top plan view of a cap portion illustrating the forward face thereof bonded with a coarse textural layer of abrasive material;

FIG. 10 is a top plan view of a cap portion illustrating the forward face thereof bonded with a medium textural layer of abrasive material;

FIG. 11 is a top plan view of a cap portion illustrating the forward face thereof bonded with a fine textural layer of abrasive material;

FIG. 21 is a left side perspective view of the dermabrasive device illustrating the shield adjustment mechanism; and FIG. 22 is a right side perspective view of the dermabrasive device illustrating the locking knob component of the shield adjustment mechanism.

DESCRIPTION OF THE PREFERRED EMBODIMENT

1. Detailed Description of the Figures

Figure 1:
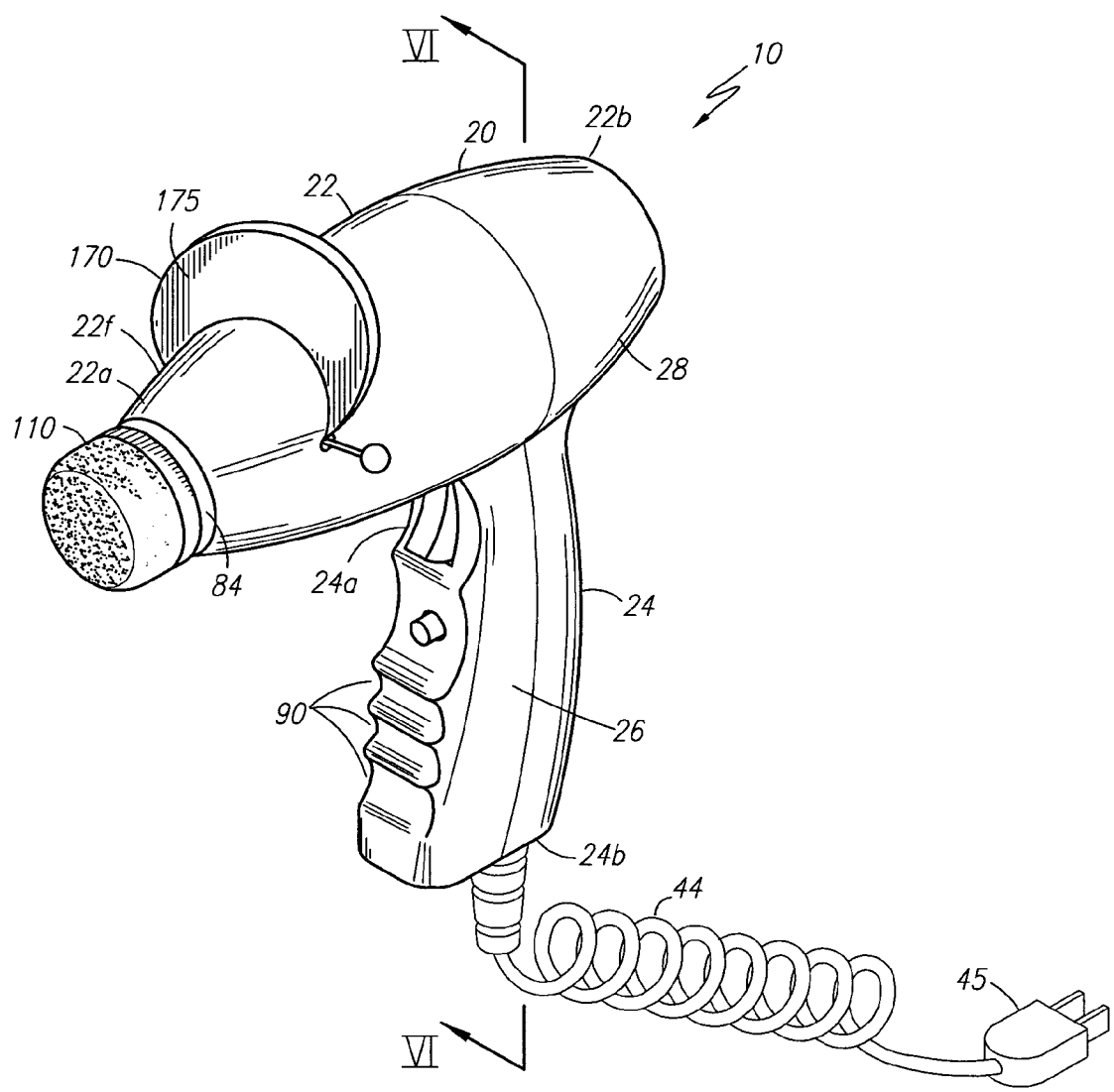
FIG. 1 is a perspective view of a dermabrasive device, according to the preferred embodiment of the present invention.
Figure 12:
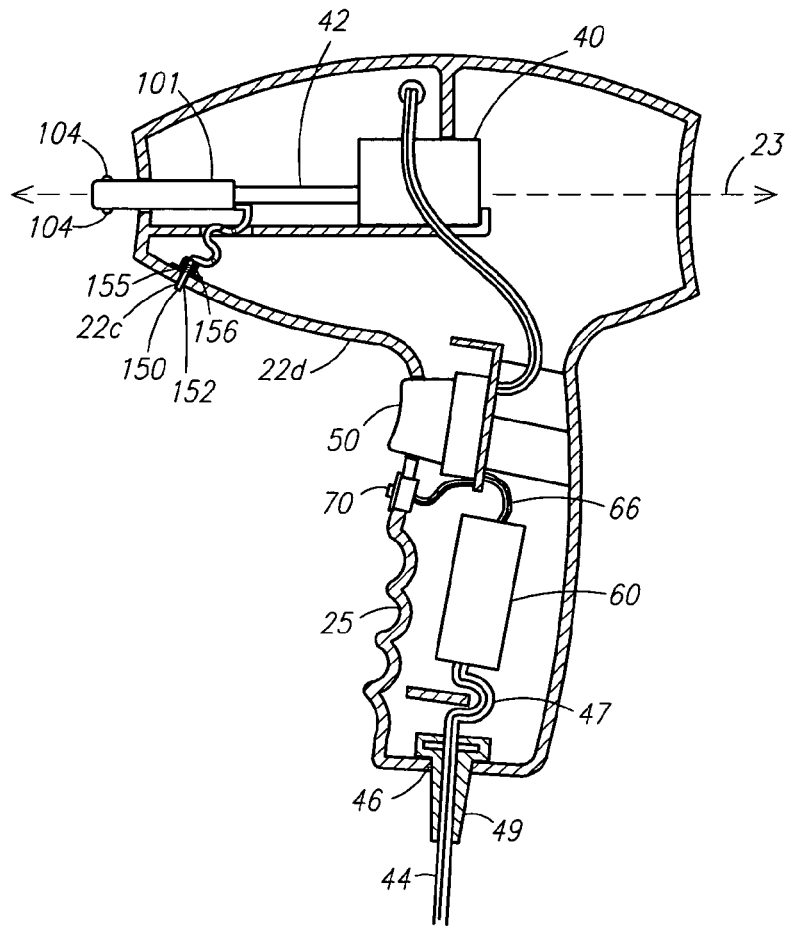
FIG. 12 is a cross-sectional view of the alternate embodiment illustrating interior components.
Figure 13:
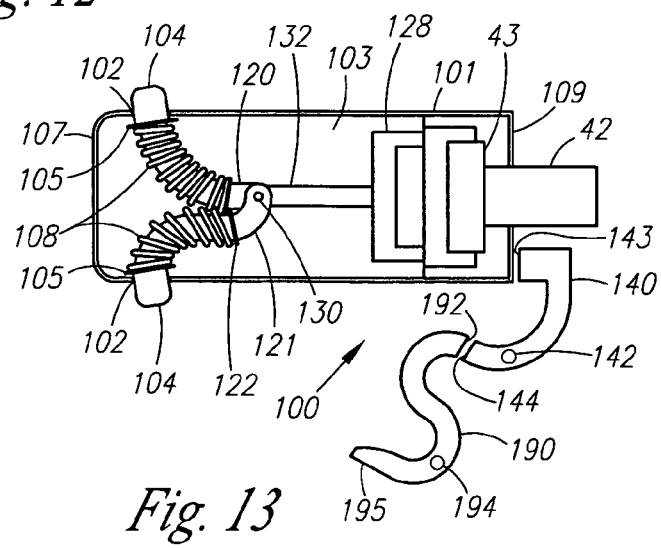
FIG. 13 is a cross-sectional view of the hub illustrating the push-button release mechanism, according to the alternate embodiment of the present invention.

Referring now to FIGS. 1-5, a dermabrasive device 10 is shown, according to the present invention, adapted to gently and painlessly remove keratinized epidermal portions of the hands and feet in a manner which is quick, easy, and efficient. The dermabrasive device 10 comprises a portable housing 20 constructed of a lightweight, rigid material. The housing 20 includes a barrel portion 22 and a handle 24 which are formed by a pair of abutting housing members 26 and 28, respectively, being connected by a fastening means 30 such as a screw 32 or bolt which extends into apertures 29a, 29b of abutting house member 28 and threadedly engage threaded openings 27a, 27b in extensions 26a, 26b of abutting house member 26. The barrel portion 22 and handle 24 each includes an anterior end 22a, 24a and a posterior end 22b, 24b respectively.

The posterior end 22b of barrel portion 22 includes an inlet opening 80 as shown in FIG. 2. The inlet opening 80 is covered by screen 82 suitably mounted thereover. The screen 82 is adapted to prevent entry of objects and debris within an interior of dermabrasive device 10. The anterior end 22a of barrel portion 22 includes an outlet opening 84.

The handle 24 includes finger-gripping channels 90 molded integral therein and being adapted for engagement by the fingers of a user.

The housing 20 is constructed so as to be available in a variety of colors.

Figure 14:
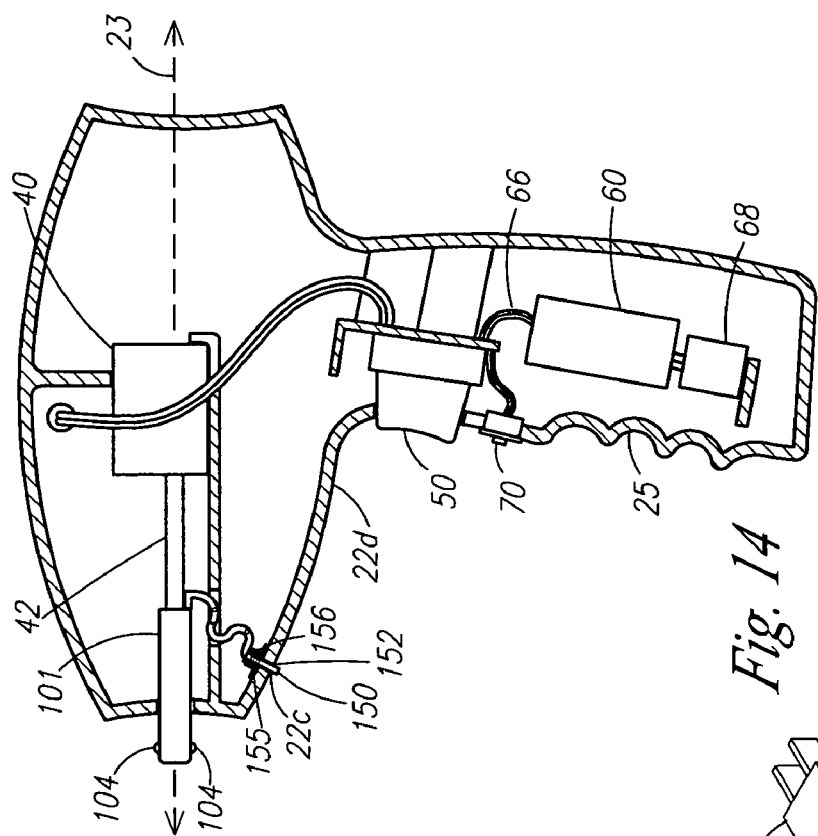
FIG. 14 is a cross-sectional view substantially similar to FIG. 12 illustrating a rechargeable battery for use as an alternative power source.
Figure 15:
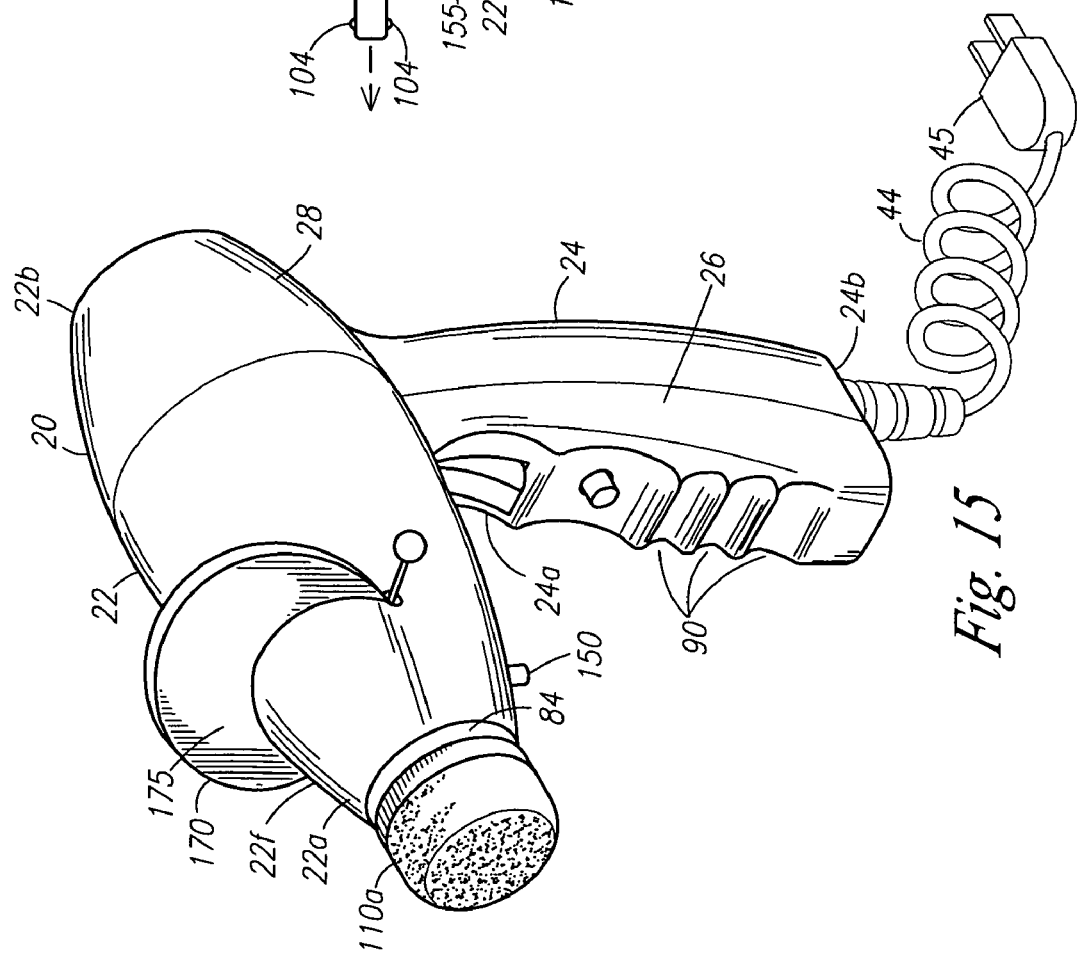
FIG. 15 is a perspective view of the alternate embodiment illustrating the location of the cap release button on the barrel portion.

Referring now to FIGS. 3 and 6, an electric drive motor 40 is fixedly set along a central axis 23 of the barrel portion 22. The electric drive motor 40 rotatably drives a plurality of removably attachable heads 110 (to be described later in greater detail). A drive shaft 42 integrally and axially extends from the drive motor 40. Electric drive motor 40 is driven by electric power supplied from a plug socket (not shown) through a power cord 44 carrying a plug 45, wherein said power cord 44 enters the posterior end 24b of handle 24 through an opening 46. The power cord 44 is provided with a strain relief 49 suitably attached within the interior of handle 24 along the posterior end 24b thereof. The power cord 44 terminates in insulated lead wires 47 or conductors which extend into a ground fault circuit interrupter 60. Alternatively, electric drive motor 40 is driven by a rechargeable battery 68 set within handle 24, as shown in FIG. 14.

An On/Off switch 50 is provided on the sidewall 25 of handle 24 for actuating electric drive motor 40.

The dermabrasive device 10 includes a ground fault circuit interrupter 60 and a controller switch 70, wherein controller switch 70 is provided on the sidewall 25 of handle 24. Controller switch 70 is positioned below On/Off switch 50 and includes a manual speed selector 72 adapted to allow a user to manually control RPM speed of electric drive motor 40. The manual speed selector 72 has multiple settings such as low, medium, and high that can be selected by user to designate speed preference. The ground fault circuit interrupter 60 is connected to power cord 44 by sealed twin conductors 47, and wherein ground fault circuit interrupter 60 is adapted so that when ground fault circuit interrupter 60 is in an open or closed position, there is no risk of electrocution in the event dermabrasive device 10 is accidentally immersed in water. Leads 66 extend from ground fault circuit interrupter 60 and connect to On/Off switch 50, controller switch 70, and electric drive motor 40.

Referring now to FIGS. 1, 3, 4, and 6-11, an end of drive shaft 42 is mounted with a head receiving component 300 adapted to allow for the removable attachment of a plurality of heads 110 thereto. Each of the plurality of heads 110 is disposable and includes a circular cap portion 112 having a forward face 113 from which a sidewall 115 extends vertically therefrom about an entire perimeter 114 of forward face 113 and terminating into an underside 116 and an inner circular cavity 117. The perimeter 114 of the forward face 113 defines a smooth, rounded edge 114a. A layer of abrasive material 118 is bonded to the forward face 113 of cap portion 112 and which extends downward a distance along the sidewall 115 thereof. Abrasive material 118 is defined of various abrasive textures which includes coarse 118a, medium 118b, and fine 118c. Thus, the plurality of heads 110 includes at least one cap portion 112 bonded with a coarse texture 118a, at least one cap portion 112 bonded with a medium texture 118b, and at least one cap portion 112 bonded with a fine texture 118c.

The head receiving component 300 is defined of a circular configuration and having a face 301 and an outer, elongated circumferential sidewall 302 extending downwardly therefrom. The cap portion 112 is adapted to mate with head receiving component 300 in a manner such that the outer, elongated circumferential wall 302 of head receiving component 300 is inserted within the inner circular cavity 117 and the head receiving component 300 is held snugly therein via frictional fit or mechanical interference. Thus, the cap portion 112 is removably secured to head receiving component 300 via frictional fit.

Referring now to FIGS. 12-15, an alternate embodiment of the present invention is disclosed, wherein an end of drive shaft 42 is mounted with a hub 101. Hub 101 is mounted to drive shaft 42 in a manner allowing for hub 101 to rotate upon actuation of drive motor 40 and to reciprocate longitudinally about the central axis 23 when drive motor 40 is arrested. Hub 101 includes an anterior end 107 and a posterior end 109. Hub 101 is adapted so as to allow for the removable attachment of a plurality of heads 110a thereto. Each of the plurality of heads 110a are disposable and includes a circular cap portion 112a having a forward face 113a from which a sidewall 115a extends vertically therefrom about an entire perimeter 114a of forward face 113a and terminating into an underside 116a. The perimeter 114a of the forward face 113a defines a smooth, rounded edge 114b. A layer of abrasive material 118 is bonded to the forward face 113a of cap portion 112a. Abrasive material 118 is defined of various abrasive textures which includes coarse 118a, medium 118b, and fine 118c. Thus, the plurality of heads 110a includes at least one cap portion 112a bonded with a coarse texture 118a, at least one cap portion 112 bonded with a medium texture 118b, and at least one cap portion 112 bonded with a fine texture 118c.

In order to facilitate removable attachment of cap portion 112a to hub 101, attention is directed to FIGS. 12-17, wherein cap portion 112a is provided with a plurality of spline receiving recesses 160. The plurality of spline receiving recesses 160 are defined along the underside 116a of cap portion 112a being spatially aligned about a periphery of a central drive shaft receiving cavity 162. The spline receiving recesses 160 are sizably adapted to receive splines 104 (to be described later in greater detail) of hub 101 in a tight, snap-fit manner, thereby locking cap portion 112a to hub 101.

Referring now more specifically to FIGS. 12-15, in order to release cap portion 112a from hub 101, a push-button release mechanism 100 is provided. The push-button release mechanism 100 is operationally and mechanically configured and adapted such that depression of a cap release button 150 facilitates retraction of splines 104 into hub 101, thereby allowing the release and removal of cap portion 112a from hub 101.

The components comprising the push-button release mechanism 100 are slidably and snugly retained within an elongated cavity 103 formed within an interior of hub 101. The push-button release mechanism 100 comprises a cap release button 150 which projects through an opening 22c formed in a sidewall 22d of barrel portion 22 along an underside thereof. The push-button release mechanism 100 further comprises a plurality of splines 104 projecting radially through openings 102 formed in the external circumferential surface of hub 101. Each spline 104 further comprises a stop flange 105 mounted therebelow. Each spline 104 further comprises an arcuate-shaped arm 120, 121 which includes a stop flange 122. Stop flange 105 of spine 104 is connected to stop flange 122 of arm 120, 121 via a spring 108 being suitably disposed therebetween. The arcuate-shaped arms 120, 121 are hingedly attached at lower ends thereof via a fastener 130. In a resting position, the splines 104 are biased via spring 108 so as to project outwardly from openings 102 in hub 101. An elongated connecting member 132 mounts arms 120 and 121 to a drive shaft hub 43 via bracket 128.

The push-button release mechanism 100 further comprises a first lever 140 defined of a generally C-shaped configuration which is pivotally mounted to an inner sidewall of the elongated cavity 103 of hub 101 via a suitable fastener 142.

An end of first lever 140 includes a lower contacting surface 144 against which an upper contacting surface 192 of a second lever 190 is adapted to engage. The second lever 190 is pivotally mounted via a suitable fastener 194 to the inner sidewall of elongated cavity 103 adjacent first lever 140. The second lever 190 includes a lower contacting surface 195 against which a stem 152 of cap release button 150 engages upon depression of cap release button 150. The stem 152 of cap release button 150 negotiates through an elongated extension 156 formed in barrel portion 22. The stem 152 is suitably disposed with a spring 155 being mounted to elongated extension 156 of barrel portion 22 so as to bias cap release button 150 outwardly in a manner such that cap release button 150 projects through opening 22c formed in the sidewall 22d of barrel portion 22 while in a resting position.

Upon depression of cap release button 150, the stem 152 thereof engages the lower contacting surface 195 of second lever 190 causing second lever 190 to pivot, whereupon upper contacting surface 192 of second lever 190 engages lower contacting surface 144 of first lever 140 causing first lever 140 to pivot, thereby causing upper contacting surface 143 of first lever 140 to engage an end of hub 101 along the posterior end 109 thereof. Engagement by first lever 140 against hub 101 facilitates slight forward longitudinal movement by hub 101, while elongated connecting member 132 remains stationary, thereby facilitating retraction of splines 104 into hub 101 cavity 103 via a tensile force applied to arms 120 and 121 through elongated connecting member's 132 attachment to drive shaft hub 43 via bracket 128 as hub 101 is urged forwardly. Retraction of splines 104 into hub 101 facilitates withdrawal of splines 104 from spline receiving recesses 160 of cap portion 112a, thereby facilitating quick release and removal of cap portion 112a from hub 101.

Figure 16:
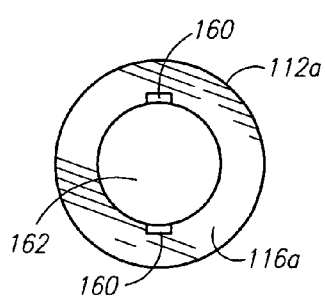
FIG. 16 is a bottom plan view of the cap portion, according to the alternate embodiment of the present invention.
Figure 17:
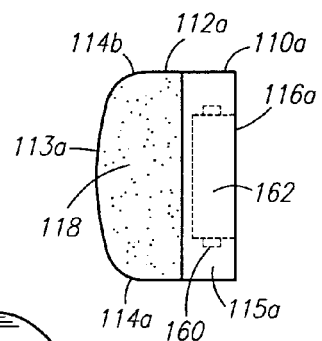
FIG. 17 is a side elevational view of the cap portion, according to the alternate embodiment of the present invention.
Figure 18:
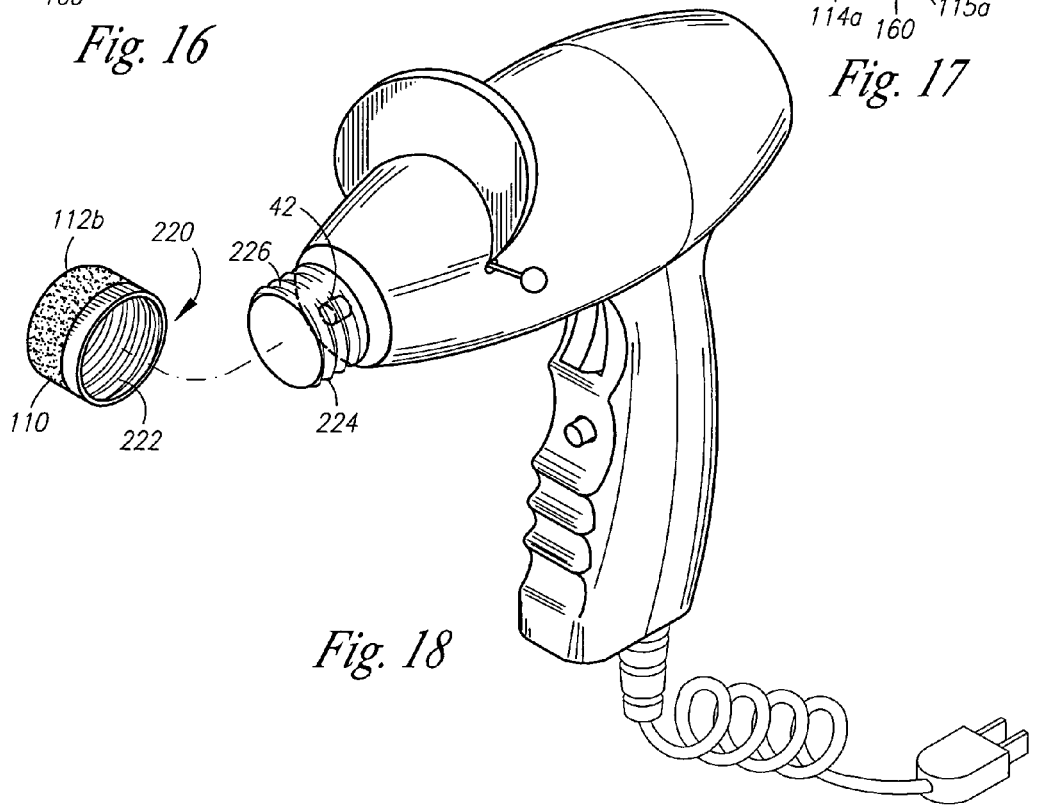
FIG. 18 is a partially exploded side perspective view of another alternate embodiment of the dermabrasive device illustrating a twist-and-lock mechanism for removably attaching heads to drive shaft.
Figure 19:
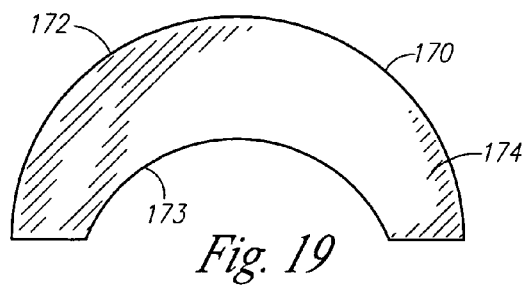
FIG. 19 is a front elevational view of the protective shield, according to the preferred embodiment of the present invention.
Figure 20:
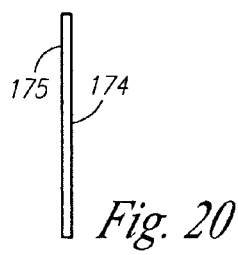
FIG. 20 is a side elevational view thereof.

It is contemplated that heads 110 may be removably attached to drive shaft 42 using other suitable attachment means or mechanisms which are adapted to facilitate both lock and release of heads 110 to and from a head receiving component, such as a twist-and-lock mechanism 220 as shown in FIG. 16. The twist-and-lock mechanism 220 comprises a cap portion 112b which includes female threads 222 adapted to threadedly engage and lockingly mate with a cap receiving component 224 having male threads 226. The cap receiving component 224 is mounted to a forward end of drive shaft 42.

Referring now to FIGS. 1, and 16-19, a disposable, protective shield 170 is provided. The protective shield 170 is adapted to shield user against contact from flakes of flying or ejected epidermis or other detritus as user operates the present invention. The protective shield 170 is further adapted so as to be angularly adjustable. Protective shield 170 is angularly adjusted via a shield adjustment mechanism 179. The protective shield 170 is defined of an arcuate shape having a narrow width and includes an upper portion 172 and a lower portion 173. Upper portion 172 is defined as having a convex curvature and lower portion 173 is defined as having a concave curvature. The protective shield 170 further includes a face 174 and a backside 175. The protective shield 170 is constructed of a lightweight, flexible material which is envisioned to be transparent or available in a variety of colors. Protective shield 170 is also envisioned to be constructed so as to be color-coordinated with portable housing 20. The protective shield 170 is adapted to be slidably inserted and held within a receiving sleeve 180.

The shield adjustment mechanism 179 comprises a receiving sleeve 180, wherein receiving sleeve 180 is pivotally mounted atop barrel portion 22 via a rotatable shaft 200 which extends through sidewall 22d and sidewall 22e of barrel portion 22. Lower ends of receiving sleeve 180 are suitably mounted to ends of rotatable shaft 200. One end of rotatable shaft 200 is mounted with a handle 204 proximal to the lower end of receiving sleeve 180. Handle 204 is adapted to facilitate angular manipulation or adjustment of receiving sleeve 180. Handle 204 rotates in a clockwise and counterclockwise direction via rotatable shaft 200, thereby allowing for the angular adjustment of shield 170. Rotatable shaft 200 is lockable to fixed position via a locking knob 210. The locking knob 210 threadedly engages an end of rotatable shaft 200 opposing handle 202. Locking knob 210 is tightened to a degree such that rotation by rotatable shaft 200 along its rotation axis is prevented. Thus, the locking knob 210 allows for shield 170 to be locked at a selected angular position according to user preference. Loosening locking knob 210 allows rotatable shaft 200 to freely rotate along its rotation axis.

The receiving sleeve 180 includes an arcuate-shaped, narrow slot 182 sizably adapted to accommodate the lower portion 173 of shield 170 in a snug, friction-fit manner. The narrow slot 182 defines a depth allowing for a majority portion of protective shield 170 to project upwardly from an upper surface 22f of barrel portion 22 after insertion of shield 170 within receiving sleeve 180. In such arrangement, the backside 175 of protective shield 170 provides a sizable surface area against which epidermal flakes are deflected, thereby preventing flake contact with user.

2. Operation of the Preferred Embodiment

To use the present invention, user selects a cap portion 112 according to the degree of abrasive texture required or desired. User next removably secures selected cap portion 112 to head receiving component 300. Next, user turns the manual speed selector 72 to a selectively-desired optimum speed preference. User then plugs plug 45 into a plug socket. User slidably inserts the lower portion 173 of the protective shield 170 into the receiving sleeve 180 within which protective shield 170 is held in a snug, friction-fit manner. Next, user angularly adjusts the protective shield 170 via the handle 204 of the shield adjustment mechanism 179 according a desired angular degree. User locks the protective shield 170 in such desired angular position by tightening locking knob 210 to a degree such that rotation by rotatable shaft 200 along its rotation axis is prevented. User next manipulates the On/Off switch 50 located on the sidewall 25 of handle 24 in order to actuate electric drive motor 40. Thereafter, user brings the cap portion 112 of dermabrasive device 10 into contact with a desired area of a foot or a hand having a target callus or target corn while gripping the handle 24 in one hand. The backside 175 of protective shield 170 provides a sizable surface area against which epidermal flakes are deflected, thereby preventing flake contact with user. User may readjust the rpm speed of electric drive motor 40 by manipulating the manual speed selector 72 according to user preference. After the epidermis of the desired area of a foot or hand is removed to a desired thickness, user removes the cap portion 112 of dermabrasive device 10 from the epidermis. User then deactivates electric drive motor 40 by manipulating the On/Off switch 50. User unplugs plug 45 from plug socket, removes protective shield 170 from receiving sleeve 180, and removes cap portion 112 from head receiving component 300. Finally, user properly disposes of protective shield 170 and cap portion 112 in an environmentally sound manner.

The use of the present invention allows for calluses on the palms of the hand and soles of the feet to be gently and painlessly removed in a manner which is quick, easy, and efficient.

Therefore, the foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be broadly limited only by the following Claims.

What is claimed is:

1. A dermabrasive device comprising:
   a portable housing, said portable housing is constructed of a lightweight, rigid material, said housing includes a barrel portion and a handle, said barrel portion and said handle are formed by a pair of abutting housing members, said barrel portion and said handle each includes an anterior end and a posterior end, wherein said posterior end of said barrel portion includes an inlet opening which is covered by a screen being suitably mounted over said inlet opening, said anterior end of said barrel portion includes an outlet opening;
   an electric drive motor, said electric drive motor is fixedly set along a central axis of said barrel portion;
   a drive shaft, said drive shaft integrally and axially extends from said electric drive motor, said drive shaft having an end mounted with a head receiving component, said electric drive motor is driven by electric power supplied from a plug socket through a power cord carrying a plug, wherein said power cord enters said posterior end of said handle through an opening, said power cord is provided with a strain relief suitably attached within an interior of said handle along said posterior end thereof, said power cord terminates in insulated lead wires which extend into a ground fault circuit interrupter,
   a plurality of heads, said plurality of heads are adapted for removable attachment to said head receiving component, said plurality of heads is rotatably driven by said electric drive motor;
   an On/Off switch, said On/Off switch is provided on a sidewall of said handle, said On/Off switch is adapted to actuate said electric drive motor;
   a controller switch, said controller switch is provided on said sidewall of said handle below said On/Off switch, wherein said controller switch includes a manual speed selector adapted to allow a user to manually control RPM speed of said electric drive motor, said manual speed selector comprises multiple settings selectable by the user to designate speed preference; and
   a layer of abrasive material, said layer of abrasive material is bonded to a forward face of each of said plurality of heads, said abrasive material extends downward a distance along a sidewall of each of said plurality of heads.

2. The dermabrasive device of claim 1, further comprising a protective shield adapted to shield user against contact from flakes of flying or ejected epidermis or other detritus, said protective shield is slidably inserted and held within a shield adjustment mechanism mounted atop said barrel portion.

3. The dermabrasive device of claim 2, wherein said protective shield is adapted so as to be angularly adjustable.

4. The dermabrasive device of claim 2, wherein said protective shield is defined as having an arcuate shape and a narrow width, said protective shield includes an upper portion and a lower portion, said upper portion is defined as having a convex curvature, said lower portion is defined as having a concave curvature, said protective shield includes a face and a backside, and wherein said protective shield is constructed of a lightweight, flexible material, said protective shield is disposable.

5. The dermabrasive device of claim 2, wherein said shield adjustment mechanism comprises a receiving sleeve, wherein said receiving sleeve is pivotally mounted atop said barrel portion via a rotatable shaft, said rotatable shaft extends through opposing sidewalls of said barrel portion, said receiving sleeve has lower ends suitably mounted to ends of said rotatable shaft, one end of said rotatable shaft is mounted with a handle being proximal to the lower end of said receiving sleeve, said handle facilitates angular manipulation or adjustment of said receiving sleeve, said handle rotates in a clockwise and counterclockwise direction via said rotatable shaft, thereby allowing for angular adjustment of said protective shield.

6. The demabrasive device of claim 5, wherein said rotatable shaft is lockable to fixed position via a locking knob, said locking knob is adapted to allow said protective shield to be locked at a selected angular position according to user preference.

7. The dermabrasive device of claim 5, wherein said receiving sleeve includes an arcuate-shaped, narrow slot sizably adapted to accommodate said lower portion of said protective shield in a snug, friction-fit manner, said narrow slot defines a depth allowing for a majority portion of said protective shield to project upwardly from an upper surface of said barrel portion after insertion of said protective shield within said receiving sleeve.

8. The dermabrasive device of claim 1, wherein said handle includes finger-gripping channels molded integral therein.

9. The dermabrasive device of claim 1, wherein said portable housing is constructed so as to be available in a variety of colors.

10. The dermabrasive device of claim 2, wherein said protective shield is transparent.

11. The dermabrasive device of claim 2, wherein said protective shield is constructed so as to be available in a variety of colors.

12. The dermabrasive device of claim 1, wherein each of said plurality of heads is disposable and includes a circular cap portion having a forward face from which a sidewall extends vertically therefrom about an entire perimeter of said forward face and terminating into an underside and an inner circular cavity, said perimeter of said forward face defines a smooth, rounded edge, wherein said drive shaft having an end mounted with a head receiving component adapted to allow for removable attachment of said plurality of heads thereto, said head receiving component is defined of a circular configuration and having a face and an outer, elongated circumferential sidewall extending downwardly therefrom, said circular cap portion is adapted to mate with said head receiving component in a manner such that said outer, elongated circumferential sidewall of said head receiving component is inserted within said inner circular cavity of said circular cap portion and said head receiving component is held snugly therein via frictional fit.

13. The dermabrasive device of claim 12, wherein said forward face of said circular cap portion is bonded with a layer of abrasive material which extends downward a distance along said sidewall of said circular cap portion, said abrasive material is available in a variety of abrasive textures.

14. The dermabrasive device of claim 13, wherein said plurality of heads includes at least one circular cap portion bonded with said abrasive material having a coarse texture, at least one circular cap portion bonded with said abrasive material having a medium texture, and at least one circular cap portion bonded with said abrasive material having a fine texture.

15. A dermabrasive device comprising:
a portable housing, said portable housing is constructed of a lightweight, rigid material, said housing includes a barrel portion and a handle, said barrel portion and said handle are formed by a pair of abutting housing members, said barrel portion and said handle each includes an anterior end and a posterior end, wherein said posterior end of said barrel portion includes an inlet opening which is covered by a screen being suitably mounted over said inlet opening, said anterior end of said barrel portion includes an outlet opening;
an electric drive motor, said electric drive motor is fixedly set along a central axis of said barrel portion;
a drive shaft, said drive shaft integrally and axially extends from said electric drive motor, said drive shaft having an end mounted with a hub, said hub is mounted to said drive shaft in a manner allowing for said hub to rotate upon actuation of said drive motor, said hub includes an anterior end and a posterior end, said hub includes openings formed in an external circumferential surface thereof throughwhich a plurality of splines projecting radially, wherein each spline of said plurality of splines comprises a stop flange mounted therebelow, and wherein each said spline further comprises an arcuate-shaped arm which includes a stop flange, said stop flange of each respective said spine is connected to a respective said stop flange of each said arm via a spring being suitably disposed therebetween, each said arcuate-shaped arm is hingedly attached to one another at lower ends thereof via a fastener, and where in a resting position, said splines are biased via said spring so as to project outwardly from said openings in said hub, said arcuate-shaped arms are mounted to said drive shaft hub by an elongated connecting member coupled to a bracket being mounted to said drive shaft hub, said electric drive motor is driven by electric power supplied from a plug socket through a power cord carrying a plug, wherein said power cord enters said posterior end of said handle through an opening, said power cord is provided with a strain relief suitably attached within an interior of said handle along said posterior end thereof, said power cord terminates in insulated lead wires which extend into a ground fault circuit interrupter;
a plurality of heads, said plurality of heads are adapted for removable attachment to said hub, said plurality of heads are rotatably driven by said electric drive motor, said plurality of heads is disposable and each of said plurality of heads includes a circular cap portion having a forward face from which a sidewall extends vertically therefrom about an entire perimeter of forward face and terminating into an underside and an inner circular cavity;
an On/Off switch, said On/Off switch is provided on a sidewall of said handle, said On/Off switch is adapted to actuate said electric drive motor;
a controller switch, said controller switch is provided on said sidewall of said handle below said On/Off switch, wherein said controller switch includes a manual speed selector adapted to allow a user to manually control RPM speed of said electric drive motor, said manual speed selector comprises multiple settings selectable by the user to designate speed preference;
a layer of abrasive material, said layer of abrasive material is bonded to said forward face of each of said plurality of heads, said abrasive material extends downward a distance along a sidewall of said head; and
a push-button release mechanism, said push-button release mechanism is operationally and mechanically adapted to facilitate release and removal of each of said plurality of heads from said hub upon depression of a cap release button.

16. The dermabrasive device of claim 15, further comprising a protective shield adapted to shield user against contact from flakes of flying or ejected epidermis or other detritus, said protective shield is slidably inserted and held within a shield adjustment mechanism mounted atop said barrel portion.

17. The dermabrasive device of claim 15, wherein said cap portion is provided with a plurality of spline receiving recesses, said cap portion includes a central drive shaft receiving cavity, said plurality of spline receiving recesses are defined along said underside of said cap portion, said plurality of spline receiving recesses are spatially aligned about a periphery of said central drive shaft receiving cavity of said cap portion, said plurality of spline receiving recesses are sizably adapted to receive said plurality of splines of said hub in a tight, snap-fit manner, thereby detachably locking said cap portion to said hub.

* * * * *